US008530191B2

(12) United States Patent
Becker et al.

(10) Patent No.: US 8,530,191 B2
(45) Date of Patent: Sep. 10, 2013

(54) METHOD FOR PREVENTING FORMATION OF TRISULFIDE DERIVATIVES OF POLYPEPTIDES

(75) Inventors: Peter Becker, Virum (DK); Thorkild Christensen, Allerød (DK)

(73) Assignee: Novo Nordisk A/S, Bagsvaerd (DK)

(*) Notice: Subject to any disclaimer, the term of this patent is extended or adjusted under 35 U.S.C. 154(b) by 83 days.

(21) Appl. No.: 12/714,900

(22) Filed: Mar. 1, 2010

(65) Prior Publication Data

US 2010/0160236 A1    Jun. 24, 2010

Related U.S. Application Data

(63) Continuation of application No. 11/813,045, filed as application No. PCT/EP2005/056976 on Dec. 20, 2005, now abandoned.

(60) Provisional application No. 60/642,628, filed on Jan. 10, 2005.

(30) Foreign Application Priority Data

Dec. 29, 2004   (DK) ................................. 2004 02022

(51) Int. Cl.
| C12N 15/18 | (2006.01) |
| C07K 1/14 | (2006.01) |
| C07K 1/34 | (2006.01) |
| A61K 38/27 | (2006.01) |
| A61P 5/06 | (2006.01) |
| C07K 14/61 | (2006.01) |

(52) U.S. Cl.
USPC ......... 435/69.4; 514/11.4; 530/397; 530/412; 930/120

(58) Field of Classification Search
None
See application file for complete search history.

(56) References Cited

U.S. PATENT DOCUMENTS

| 6,299,776 B1 | 10/2001 | McWhirter et al. |
| 7,232,894 B1 | 6/2007 | Hemmendorff et al. |
| 2004/0048315 A1 | 3/2004 | Rathore et al. |

FOREIGN PATENT DOCUMENTS

| EP | 0546393 B1 | 6/1993 |
| EP | 0608779 A1 | 8/1994 |
| EP | 1095055 B1 | 5/2001 |
| GB | 852914 | 11/1960 |
| JP | 2002-520332 | 7/2002 |
| WO | WO 94/24157 | 10/1994 |
| WO | WO 9602570 A1 | 2/1996 |
| WO | WO 00/02900 | 1/2000 |
| WO | WO 2004/031213 A1 | 4/2004 |

OTHER PUBLICATIONS

Jespersen, A.M. et al., "Characterisation of a trisulphide derivative of biosynthetic human growth hormone produced in *Escherichia coli*", Eur. J. Biochem., 1994, vol. 219, pp. 365-373.

Breton, J. et al., "Detection of traces of a trisulphide derivative in the preparation of a recombinant truncated interleukin-6 mutein", Journal of Chromatography A, 1995, vol. 709, pp. 135-146.

(Continued)

*Primary Examiner* — Zachary Howard
(74) *Attorney, Agent, or Firm* — Rosemarie R. Wilk-Orescan

(57) ABSTRACT

A method for reducing or substantially preventing formation of a trisulfide derivative of a polypeptide in a liquid medium containing the polypeptide ijn question comprises stripping the liquid medium with a gas, suitably a chemically unreactive gas such as nitrogen or argon.

3 Claims, 3 Drawing Sheets

(56) References Cited

OTHER PUBLICATIONS

Frankenne, F. et al., "The Physiology of Growth Hormones (GHs) in Pregnant Women and Partial Characterization of the Placental GH Variant", Journal of Clinical Endocrinology and Metabolism, 1988, vol. 66, No. 6, pp. 1171-1180.

Briggs, R.G. et al., "Sulfhydryl Reactivity of Human Erythrocyte Superoxide Dismutase—On the Origin of the Unusual Properties of the Protein when Prepared by a Procedure Utilizing Chloroform and Ethanol for the Precipitation of Hemoglobin", Biochimica et Biophysics Acta, 1978, vol. 537, pp. 100-109.

Bewley, T.A. et al., "The Chemistry of Human Pituitary Growth Hormone", Advances in Enzymology and Related Areas of Molecular Biology, 1975, vol. 42, pp. 73-94.

Andersson, C. et al., "Isolation and Characterization of a Trisulfide Variant of Recombinant Human Growth Hormone Formed During Expression in *Escherichia coli*", Int. J. Peptide Protein Res., 1996, vol. 47, pp. 311-321.

Pristatsky et al.; 2009; Anal Chem.; 81: 6148-6155.

Bang et al., 2004; Applied and Environmental Microbiology; 66(9): 3939-3944.

Wells; 1990; Biochemistry 29(37): 8509-8517.

Ngo et al., 1994; "The Protein Folding Problem and Tertiary Structure Prediction; Chapter 14: Computational Complexity Protein Structure Prediction, and the Levinthal Paradox"; pp. 433-440 and 492-495 only.

Bork; 2000; Genome Research; 10:398.

Skolnick et. al., 2000; Trends in Biotech; 18(1):34.

Doerks et. al., 1998; Trends in Genetics; 14(6): 248.

Brenner; 1999; Trends in Genetics; 15(4):132.

Canova-Davis et al., "Confirmation by Mass Spectrometry of a Trisulphide Variant in Methionyl Human Growth Hormone Biosynthesized in *Escherichia Coli*", Anal Chem, 1996, vol. 68, pp. 4044-4051.

METHOD FOR PREVENTING FORMATION OF TRISULFIDE DERIVATIVES OF POLYPEPTIDES

CROSS-REFERENCE TO RELATED APPLICATIONS

This application is a continuation application of U.S. patent application Ser. No. 11/813,045, filed Jun. 28, 2007, which is a 35 U.S.C. §371 national stage application of International Patent Application PCT/EP2005/056976 (published as WO 2006/069940), filed Dec. 20, 2005, which claimed priority of Danish Patent Application PA 2004 02022, filed Dec. 29, 2004; this application further claims priority under 35 U.S.C. §119 of U.S. Provisional Application 60/642,628, filed Jan. 10, 2005, herein incorporated by reference.

FIELD OF THE INVENTION

The present invention relates a method for preventing the formation of trisulfide derivatives of polypeptides during production or processing thereof in liquid media.

In particular, the invention relates to the production of a human growth hormone, or an intermediate, derivative, analog, variant or mutant thereof, which is substantially free of, or contains a reduced amount of, trisulfide derivative(s).

BACKGROUND OF THE INVENTION

A number of polypeptides containing disulfide bonds are known to form trisulfide derivatives. Among these are superoxide dismutase, interleukin mutein and growth hormone (GH). In principle, however, other polypeptides containing disulfide bonds, e.g. insulin, interleukins and certain clotting factors (such as Factor VII) can potentially form trisulfide derivatives under specific conditions.

Among the most studied polypeptides known to form trisulfide derivatives are growth hormones (GH), in particular human growth hormone. The term "human growth hormone" (hGH; sometimes also referred to, inter alia, as "somatropin" or "somatotropin") is generally understood to refer to the protein (polypeptide) hormone consisting of a single chain of 191 amino acid residues cross-linked by two disulfide bridges, the monomeric form thereof having a molecular weight of approx. 22000 (22 kDa). Growth hormone preparations isolated from human pituitary are not homogeneous. For example, a smaller (20 kDa) variant produced from the same gene is also known. The "basic hGH" variant (hGH-V) expressed by the placenta during pregnancy is another analogue/variant which is a product of a separate gene; like the 22 kDa hGH polypeptide it consists of 191 amino acid residues, but 13 amino acid residues at various positions in the sequence differ from those in 22 kDa hGH [see, e.g, Bewley et al., *Adv. Enzymol.* 42, 73-166 (1975), and Frankenne et al., J. Clin. Endocrin. and Metabol. 66, 1171-1180 (1988)].

In hGH (i.e. the 22 kDa polypeptide), four cysteine residues are present giving rise to the two disulfide bridges. The first disulfide bridge forms a major loop between Cys 53 and Cys 165, while the second one form a minor loop between Cys 182 and Cys 189. The minor loop is located at the molecule's surface, while the major loop is embedded within the hGH molecule. Trisulfide bridge formation can occur at both the minor and major loop.

Human growth hormone is essential, inter alia, for longitudinal bone growth and normal growth development during childhood. Numerous other effects or applications of hGH are known, including promotion of healing of bone fractures, breakdown of adipose tissue and minimization of post-operative fatigue syndrome.

Production of therapeutically useful polypeptides, e.g. hGH, on an industrial scale is currently usually accomplished by use of recombinant techniques. Some of the developed recombinant processes use bacterial hosts, such as different strains of *Escherichia coli*, while other processes use eukaryotic microorganisms, such as yeasts (e.g. *Saccharomyces cerevisiae*), as hosts.

After production (fermentation), the medium comprising the recombinant polypeptide is usually processed further. During such processing the polypeptide may be subjected to various extraction and purification processes, such as centrifugation, microfiltration and/or ultrafiltration.

One of the problems encountered using conventional recombinant manufacturing methods to produce polypeptides is the formation of polypeptide by-products. In the production of polypeptides containing disulfide bonds, the formation of derivatives, in particular trisulfide derivatives, can be problematical.

The trisulfide derivative in question is one wherein the peptide molecule contains an extra sulfur atom that forms a "trisulfide bridge" within the molecule. Such a trisulfide derivative has been isolated during production of growth hormone, where it constitutes an undesirable by-product.

Thus, WO 94/24157 discloses a method for detecting a hydrophobic derivative of hGH comprising an extra sulfur atom compared to native hGH. The extra sulfur atom of the hydrophobic derivative of hGH forms a "trisulfide bridge" yielding a hGH trisulfide derivative (TS-hGH). Further disclosed is a method for converting this hGH trisulfide derivative back to its native hGH form by treating the hGH trisulfide derivative with a mercapto compound, such as cysteine, glutathione, 2-mercaptoethanol or dithiothreitol.

In addition, the trisulfide derivative of hGH has been described by Andersson et al., "*Isolation and characterization of a trisulfide variant of recombinant human growth hormone formed during expression in Escherichia coli,*" Int. J. Peptide Protein Res. 47 (1996) pp. 311-321, and by A. Jesperson et al., "*Characterisation of a trisulfide derivative of biosynthetic human growth hormone produced in Escherichia coli,*" Eur. J. Biochem. 219 (1994) pp. 365-373 (1994), and trisulfide derivatives have also been reported for other peptides, viz. recombinant superoxide dismutase [Briggs et al., *Biochem. Biophys. Acta,* 537 (1978) pp. 100-109] and a mutein of interleukin [J. Breton et al., *J. Chromatoqr. A* 709 (1) (1995) pp. 135-46].

WO 96/02570 describes another method for converting the hGH trisulfide derivative back to the native form of hGH by treating the derivative with a sulfite compound, such as sodium sulfite, potassium sulfite or ammonium sulfite, or an alkaline-earth metal sulfite such as magnesium sulfite or calcium sulfite.

WO 00/02900 describes, inter alia, a method for the production of recombinant peptides with a low amount of trisulfides, characterized by the addition of a metal salt (e.g. potassium or sodium salt) during or after the fermentation step.

WO 04/31213 discloses, inter alia, a method for decreasing the amount of a trisulfide isoform impurity produced in recombinant production of a "growth hormone antagonist polypeptide" in genetically modified host cells, wherein the impurity is contacted with a "mercapto compound" (exemplified by sulfites, glutathione, β-mercapto-ethanol, dithiothreitol, cysteine and others). The application also discloses the use of chelating agents or metal salts to achieve a reduction in the amount of trisulfide formed.

BRIEF DESCRIPTION OF THE INVENTION

Figure 1:
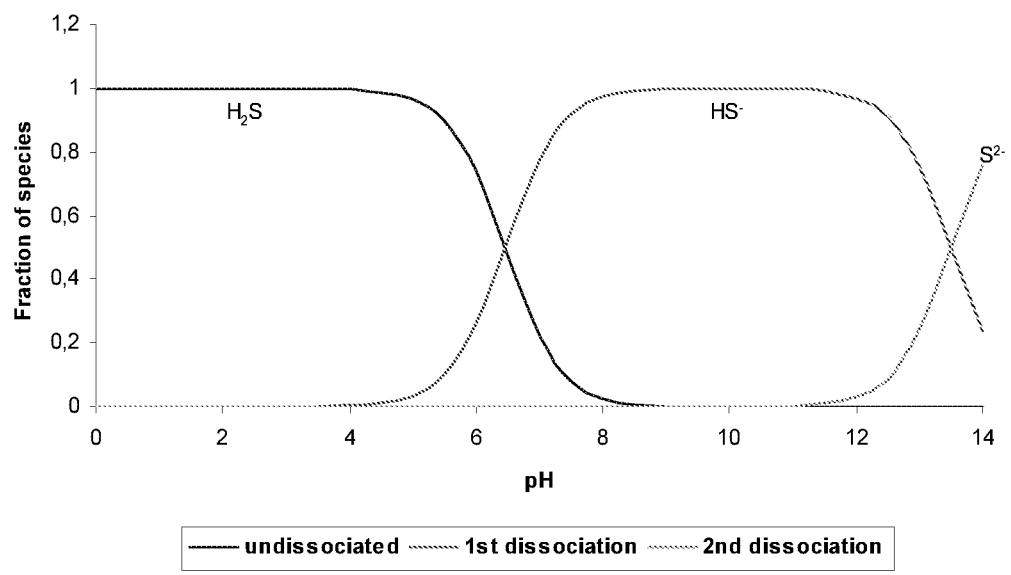
FIG. 1 shows the distribution of hydrogen sulfide species ($H_2S$, $HS^-$ and $S^{2-}$, respectively) in water at 20° C. as a function of pH.

It has surprisingly been found that formation of a trisulfide derivative of a polypeptide during production and/or processing of the polypeptide in a liquid medium can be minimized or prevented by a process in which the liquid medium is stripped with a gas, e.g. by aeration of the medium by means of passage therethrough of a stream of bubbles of the gas in question.

DETAILED DESCRIPTION OF THE INVENTION

As indicated above, one aspect of the invention relates to a method for reducing or substantially preventing formation of a trisulfide derivative of a polypeptide in a liquid medium (typically an aqueous medium) containing the polypeptide, the method comprising stripping the liquid medium with a gas.

Polypeptides

The polypeptide of interest may be of natural or synthetic origin, and the method according to the invention is thus not limited to applications to recombinant polypeptides or to polypeptides produced by other means under controlled conditions, but may potentially be applied to polypeptides extracted from any source, e.g. from a plant or an animal.

As already mentioned, a number of polypeptides are known to be prone to form trisulfide derivatives. These polypeptides, particularly therapeutic polypeptides, usually contain one or more disulfide bonds, and among these are superoxide dismutase, interleukin mutein and growth hormones (GH). In principle, other polypeptides containing disulfide bonds, e.g. insulin, can potentially form trisulfide derivatives under appropriate conditions.

Among the most studied polypeptides known to form TS derivative impurities are growth hormones (GH), and in embodiments of the invention the polypeptide of interest is a growth hormone, such as a mammalian growth hormone (e.g. human, bovine, equine, porcine, ovine, canine or feline GH), an avian GH, or GH of salmon, trout or tuna origin, particularly human growth hormone (hGH), notably recombinantly produced hGH (rhGH). The term growth hormone (GH) in the context of the invention also encompasses: truncated forms of GH, i.e. truncated forms of a growth hormone wherein one or more amino acid residues has/have been deleted; GH analogues, wherein one or more amino acid residues in the native molecule has/have been substituted with another amino acid residue, preferably a residue of a naturally occurring amino acid, as long as the substitution does not lead to any adverse effect such as antigenicity or reduced activity; and GH derivatives, e.g. deamidated or sulfoxidated forms of the growth hormone, or forms having an N- or C-terminal extension (such as Met-hGH, Met-Glu-Ala-Glu-hGH or Ala-Glu-hGH). Other GH derivatives of relevance include those in which a GH (e.g. hGH) is conjugated to a molecule such as an albumin, e.g. human serum albumin (see, e.g., WO 97/24445), or a water-soluble polymer such as a polyethyleneglycol (PEG) (see, e.g., WO 03/044056), in order to achieve, e.g., protracted duration of GH activity. As already indicated, among growth hormones per se, the preferred growth hormone in relation to treatment of humans is normally hGH [i.e. natural human growth hormone, particularly recombinantly produced human growth hormone (rhGH) which is identical to the natural hormone], and truncated forms, analogues and derivatives of hGH of the latter types are of relevance in the context of the present invention.

Stripping

In the present context, the term "stripping" refers to the displacement or removal of a volatile component (e.g. a dissolved component which in its native state under ambient conditions is a gas) from the liquid medium by means of aeration of the liquid medium with a suitable gas (vide infra) at an appropriate rate and temperature, and for an appropriate duration of time This may be done, for example, by passing the gas in question through the liquid medium (e.g. by sending a stream of gas bubbles into the medium), with or without stirring or other means of mixing, or by other means creating a large liquid phase/gas phase interface at which gas diffusion between phases may occur. In this connection, parameters which may be adjusted in order to achieve a desired stripping effect include:

- duration of contact between gas (stripping gas) and liquid medium;
- rate of introduction/passage of stripping gas into the liquid medium;
- volume of stripping gas employed;
- magnitude of surface area of contact between the gas phase and liquid phase;
- vigorousness of stirring/mixing;
- pH of the liquid medium; and
- temperature of the liquid medium and/or the stripping gas.

Hydrogen sulfide may be formed in the presence of an appropriate sulfur-containing source (e.g. a disulfide-bridge-containing polypeptide itself) in a liquid medium under appropriate redox conditions, and in relation to the present invention it is believed (vide infra) that the presence of hydrogen sulfide ($H_2S$) and/or deprotonated forms thereof (i.e. $HS^-$ and/or $S^{2-}$) plays an important role in the formation of trisulfide (TS) derivatives of polypeptides.

Figure 2:
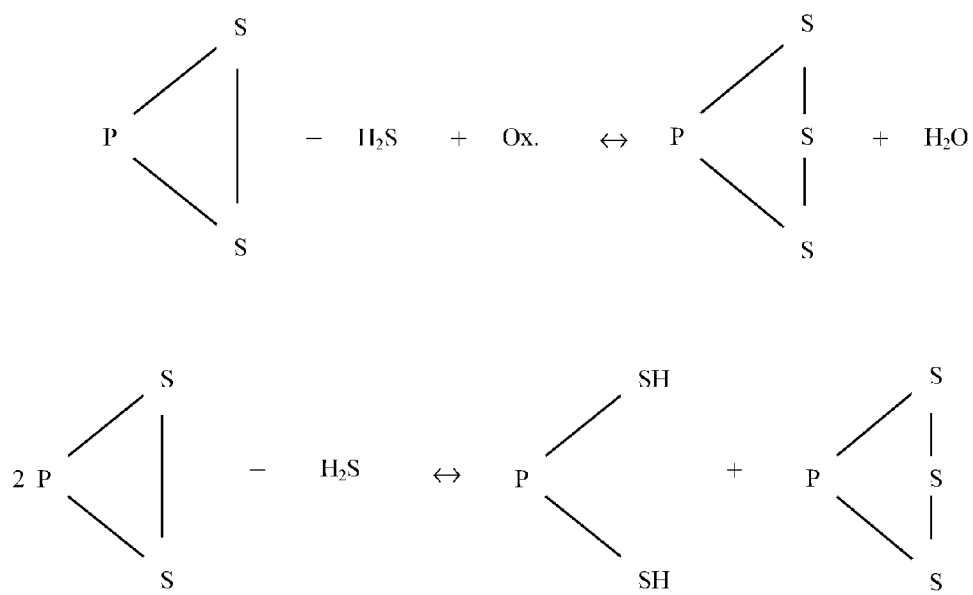
FIG. 2 show suggested mechanisms of formation of trisulfide derivatives of peptides in the presence of $H_2S$.
Figure 3:
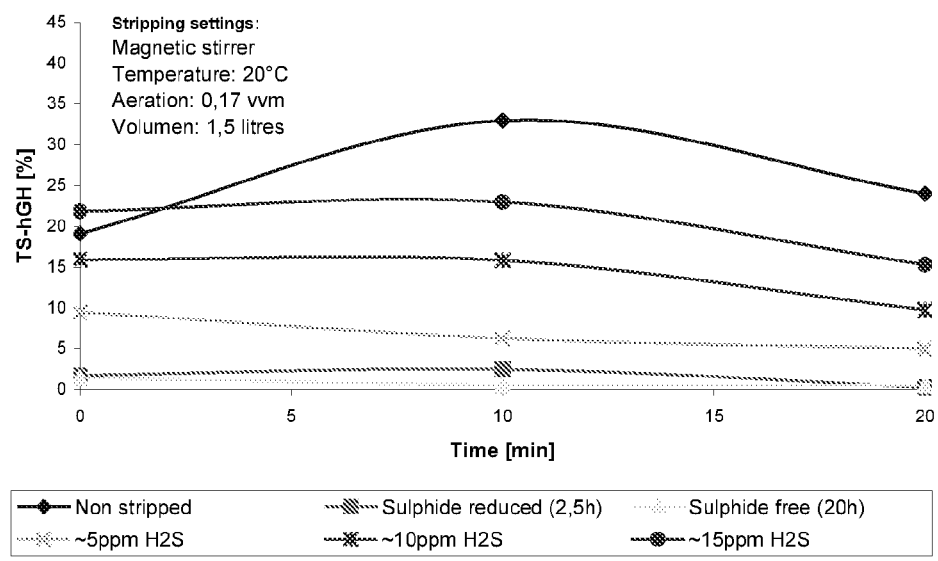
FIG. 3 show the impact of stripping on formation of TS-hGH in micro-filtered homogenate, from a batch culture producing hGH.

Without being bound by any theory, it is believed that $H_2S$ may induce the formation of TS derivatives of certain polypeptides containing disulfide bridges [e.g. growth hormones (GH), such as human growth hormone (hGH)] by one or both of the two mechanisms illustrated schematically in FIG. 2. In the first proposed mechanism (upper part of FIG. 2), an oxidizing agent (denoted "Ox."), e.g. oxygen ($O_2$), present in the solution acts by oxidation of S in $H_2S$ with attendant formation of a trisulfide bridge in the polypeptide. In the second proposed mechanism (lower part of FIG. 2), the polypeptide itself act as an oxidizing agent, forming a trisulfide bridge in the presence of $H_2S$.

Without being bound by any theory, it is believed that displacement or removal of $H_{2S}$ from the liquid medium in question may play a major role in reducing or eliminating the formation of undesired TS derivatives.

Hydrogen sulfide is a weakly acidic, moderately water-soluble gas which in aqueous solution exists in dynamic equilibrium with the anionic species $HS^-$ and $S^{2-}$, respectively. It is apparent from FIG. 1 herein (vide infra), which shows the distribution of the three species $H_2S$, $HS^-$ and $S^{2-}$, respectively, in water at 20° C. as a function of pH, that the proportion of $H_2S$ in solution is extremely small at pH values above approx. 9, and approaches 100% at a pH of approx. 4.

Given that $H_2S$ is the only one of the three species in question that exists in the gaseous state under ambient conditions, if the presence of $H_2S$ in the liquid medium is indeed of major importance in relation to formation of TS derivatives of polypeptides, then it is believed to be appropriate that stripping of the liquid medium with a gas takes place at $pH \leq 9$ in the liquid medium, such as at $pH \leq 8$, e.g. $pH \leq 6$. It should, however, be remarked that since equilibration between the three sulfide species ($H_2S$, $HS^-$ and $S^{2-}$) in solution is rapid, it should in principle be possible to perform gas stripping at a pH in excess of 9.

The choice of pH in the liquid medium during gas stripping in the manner of the invention will, of course, also be influenced by other factors, such as the stability of the polypeptide of interest towards formation of other derivatives thereof (e.g. dimers or higher oligomers thereof, deamidated forms thereof, sulfoxidated forms thereof, etc.), avoidance of precipitation, and so on.

Stripping Gas

The gas employed in stripping of the liquid medium in the manner of the invention may in principle be any gas that does not significantly react with or otherwise adversely affect the polypeptide of interest (or other central or essential components contained in the liquid medium); thus, for example, gases such as air, oxygen, nitrogen, helium, argon, carbon dioxide or combinations thereof might potentially be used according to the present invention. However, if the present inventors' belief (vide supra) that the presence of $H_2S$ in the liquid medium is of central importance in relation to formation of TS derivatives of polypeptides is correct, then those gases which are most appropriate for use in that connection are believed to be gases which are substantially chemically inert, particularly with respect to causing oxidation, reduction or other reactions, and/or influencing the pH conditions pertaining in the liquid medium, and which are readily available in substantially pure form at acceptable cost. Gases of particular relevance in this connection then include nitrogen ($N_2$) and the more abundant and readily available members of the so-called "noble gases" [which include helium (He), neon (Ne), argon (Ar), krypton (Kr) and Xenon (Xe)], notably helium and argon, particularly argon. These gases (notably $N_2$, He and Ar) are readily commercially available in a high state of purity (typically $\geq 99.8$ volume % for $N_2$, and $\geq 99.9$ volume % or higher for He and Ar) in compressed form in cylinders of varying capacity.

Trisulfide derivatives can in principle form at any stage during the production and purification of a polypeptide of the type in question. There are, however, indications that it is of greatest importance to avoid TS derivative formation during post-production purification steps, particularly filtration steps; thus, for example, in the case of recombinant human growth hormone (hGH), it appears that substantial formation of TS-hGH takes place during, in particular, filtration procedures subsequent to production per se.

The method according to the invention is particularly well suited to application subsequent to production of the polypeptide of interest (e.g. production by fermentation in a medium containing a recombinantly modified microorganism expressing the polypeptide), e.g. in conjunction with downstream (post-production) separation and/or purification steps, such as filtration, microfiltration, ultrafiltration, column separation and the like. When employed in relation to human growth hormone, the method is suitably applied during post-production procedures prior to the final purification steps.

In further embodiments of methods according to the invention, compounds that influence the stability of, or reduce the formation of undesirable derivatives of, the desired polypeptide may be added to the liquid medium in connection with post-production processing steps. Thus, for example, sulfite salts (e.g. an alkali metal sulfite such as sodium or potassium sulfite) or mercapto compounds (e.g. one or more compounds selected from the group consisting of glutathione, β-mercaptoethanol, dithiothreitol, dithioerythritol, mercaptoethylamine, cysteine and cystine) may be added to the liquid medium which is to be subjected to stripping in the manner of the invention.

Further aspects of the present invention relate to:

polypeptides that are substantially free of TS derivatives (in particular recombinant human growth hormone (rhGH) substantially free of TS-hGH derivatives), obtained or obtainable by a method according to the invention;

pharmaceutical compositions comprising such polypeptides (in particular comprising such an rhGH) together with a pharmaceutically acceptable carrier or diluent;

a method for treating a condition responsive to administration of human growth hormone, comprising administering a therapeutically effective amount of substantially TS-hGH-free rhGH according to the invention to a subject having such a condition;

and the use of substantially TS-hGH-free rhGH according to the invention in the manufacture of a medicament for the treatment of a condition responsive to administration of human growth hormone.

Pharmaceutical Administration

In relation to pharmaceutical compositions of the invention, examples of suitable carriers or diluents will be well known to persons of ordinary skill in the art.

In relation, in particular, to hGH/rhGH, the regimen for treatment of a given subject/patient with growth hormone, in the manner described herein, may be determined by one skilled in the art. The daily dose to be administered can be determined by a physician and will depend, inter alia, on the route of administration and on the age, body weight and condition of the subject or patient. A convenient daily dosage of hGH is typically in the range of from about 0.001 mg/kg body weight to about 2.0 mg/kg body weight, often from about 0.01 mg/kg body weight to about 1.0 mg/kg body weight.

Growth hormone (e.g. hGH) may be administered in a single dose or in repeated doses during the day, and administration in the manner described herein should continue until the treated individual is no longer in need of such treatment. The route of administration may be any route that effectively transports the hormone to the appropriate or desired site of action, such as by infusion (continuous or pulsatile), injection, pulmonary inhalation, or by oral or nasal administration. Presently preferred routes include parenteral routes (e.g. via intramuscular, intraperitoneal, intravenous or subcutaneous injection, or by implant). The growth hormone can be formulated in dosage forms appropriate for each route of administration. The compositions or dosage forms may be in conventional forms, e.g. aerosols, solutions or suspensions.

A GH (e.g. hGH) composition may be in a form suited for systemic injection or infusion, and may, as such, be formulated with a suitable liquid vehicle such as sterile water or an isotonic saline or glucose solution. The compositions may be sterilized by conventional sterilization techniques which are well known in the art. The resulting aqueous solutions may be packaged for use as such, or they may be filtered under aseptic conditions and lyophilized, the lyophilized preparation being combined with the appropriate sterile aqueous vehicle prior to administration. The composition may contain pharmaceutically acceptable auxiliary substances as required to approximate physiological conditions, such as buffering agents, tonicity-adjusting agents and the like. Non-limiting examples of buffering agents include citrate salts and histidine; non-limiting examples of tonicity adjusting agents include sugars, such as sucrose and mannitol, and salts, such as alkali metal and alkaline earth metal chlorides, e.g. sodium, potassium or calcium chloride, and the like. Examples of liquid carriers are syrup, peanut oil, olive oil, phospholipids, fatty acids, fatty acid amines, polyoxyethylene and water. Aqueous liquid formulations, in particular, may advantageously contain a non-ionic surfactant, e.g. a polysorbate [such as polysorbate 20 (e.g. Tween™ 20) or a poloxamer [such as poloxamer 188 (e.g. Pluronic™ F68) or poloxamer 407 (e.g. Lutrol™ F127)], and a preservative, such as benzyl alcohol, phenol or a cresol (e.g. m-cresol), will often be incorporated.

It may be advantageous to provide GH (e.g. hGH) in the form of a sustained release formulation. As such, the composition may be formulated as microcapsules or microparticles containing the growth hormone encapsulated in, or dispersed in, a suitable pharmaceutically acceptable biodegradable polymer, such as polylactic acid, polyglycolic acid or a lactic acid/glycolic acid copolymer.

For nasal administration, the GH preparation may contain growth hormone dissolved or suspended in a liquid carrier, in particular an aqueous carrier, for aerosol application. The carrier may contain additives such as solubilizing agents (e.g. propylene glycol), surfactants, absorption-enhancers such as lecithin (phosphatidylcholine) or cyclodextrin, or preservatives such as parabenes.

Growth hormone (e.g. hGH) may be formulated by any of the established methods of formulating pharmaceutical compositions, e.g. as described in *Remington: The Science and Practice of Pharmacy* (1995).

EXAMPLES

Example 1

Stripping of H$_2$S from Fermentation Broth

A sample comprising fermentation broth, recombinant microorganisms [*E. coli* containing an expression cassette comprising the gene encoding for recombinant human growth hormone (rhGH)] was taken from a hGH production batch. The sample was homogenised, and 6 sub-samples, each of 1500 ml, were introduced into 2000 ml measuring cylinders and stirred magnetically. Stripping of H$_2$S from sub-samples was performed by bubbling nitrogen gas (obtainable, for example, from Air Liquide Danmark A/S, Ballerup, Denmark; ≧99.8% purity) into each sub-sample (temperature 20° C.) at a rate of 15-20 l/hour via a silicone tube extending to the bottom of the measuring cylinder. Sub-sample 1 was not stripped (control), sub-sample 2 was subjected to stripping for 2.5 hours, while sub-samples 3, 4, 5 and 6 were subjected to stripping for 20 hours.

After gas-stripping in this manner, the sub-samples were purified using a laboratory-scale microfiltration system [Millipore Labscale™ TFF system using modified polyethersulfone (BIOMAX™-1000) membranes], resulting in very low TS-hGH formation in the collected permeate. However, in the case of sub-samples 4, 5 and 6, sodium sulfide (Na$_2$S) was added to concentrations of approx. 5, 10 and 15 ppm, respectively, prior to microfiltration.

Determination of hGH

The amount of hGH in the microfiltered sub-samples was measured using an hGH-directed ELISA-method: In this method a polyclonal guinea pig antibody directed against human growth hormone is bound to a microtest plate. This antibody (coating antibody) reacts with growth hormone from the samples. A peroxidase-labelled polyclonal guinea pig antibody (detection antibody) directed against hGH then reacts with the now fixed growth hormone. On adding enzyme substrate (peroxidase substrate), the peroxidase activity in the peroxidase-labelled antibody results in development of a colour with intensity proportional to the concentration of growth hormone in the sample. The reaction is stopped by addition of acid, and the absorbance is read in a photometer at 450 nm, as well as at a reference wavelength of 620 nm.

Determination of TS-hGH

Levels of TS-hGH were determined by hydrophobic interaction chromatography (HIC): Optimised measurement conditions had been found to be obtained at an approximate hGH concentration in the sample of 0.71 g l$^{-1}$, and samples were therefore diluted to adjust them to this particular hGH concentration. The initial hGH-concentration is determined from an absorbance measurement at 277 nm according to the equation:

$$c_{hGH} = \text{Absorbance (277 nm)} * 0.82 \quad \text{(in g l}^{-1}\text{)}$$

A total volume of 15 µl of adjusted sample was applied to a 200 mm long and 4.6 mm wide column. Gradient elution with the following two eluents:
A: 1M (NH$_4$)$_2$SO$_4$; 0, 1 M Na$_2$HPO$_4$; pH 6.5
B: 0, 1 M Na$_2$HPO$_4$; 5% v/v CH$_3$CN; pH 6.5
was then carried out as summarized in the following table:

| Flow [ml/min] | Total time [min] | Eluent A [%] | Eluent B [%] |
|---|---|---|---|
| 0.5 | 0.0 | 70 | 30 |
| 0.5 | 8.0 | 45 | 55 |
| 0.5 | 35.0 | 0 | 100 |
| 0.5 | 45.0 | 0 | 100 |
| 0.5 | 45.1 | 70 | 30 |
| 0.5 | 70.0 | 70 | 30 |
| 0.5 | 73.0 | 70 | 30 |
| 0.05 | 73.5 | 0 | 100 |
| | Total: 73.5 | | |

Other conditions were as follows:
Temperature, adjusted sample: 2° C.-8° C.
Temperature, column heater: 28° C.±2° C.
Wavelength, UV-detection: 220 nm The relative amount of TS-hGH (in weight percent) in the investigated sample is then obtained from the following equation:

$$TS - hGH\ [\%] = \frac{Area_{TS-hGH} \cdot 100}{Area_{TS-hGH} + Area_{hGH}}$$

This procedure gives a limit of quantification (LOQ) of 20 ng TS-hGH contained in the investigated sample. To verify the measured results for the samples, a standard is measured at the beginning of each series and also at the end of each series.

Determination of H$_2$S

Hydrogen sulfide concentrations in liquid samples were determined using the MERCK Spectroquant™ quick-test. This test is designed to measure all sulfide species dissolved in aqueous samples in a concentration span from 0.03 to 3.3 ppm using photometric analysis. The test kit contains three different reagents that cause a colour reaction: Hydrogen sulfide reacts with N,N'-dimethyl-1,4-phenylenedi-ammonium dichloride (Re-agent 2) to give colourless leucomethylene blue, which is then oxidised by ferric sulfate (Reagent 3) to methylene blue. Sulfamic acid (Reagent 1) prevents interference from nitrite. The colour reaction generating methylene blue results in a pronounced absorption maximum at 665 nm, with blanks showing practically no absorbance at this wavelength. For measurement of $H_2S$ levels in unfiltered fermentation broth, the broth was centrifuged (10 min, 5000 rpm) after addition of the three reagents. $H_2S$ standard solutions of known concentration were used for calibration.

Results are shown in Table 1, below.

TABLE 1

| Filtration time (min) | hGH (mg/l) | TS-hGH (%) | $H_2S$ (ppm) | hGH (mg/l) | TS-hGH (%) | $H_2S$ (ppm) | hGH (mg/l) | TS-hGH (%) | $H_2S$ (ppm) |
|---|---|---|---|---|---|---|---|---|---|
| | (1) Non-stripped | | | (2) Sulfide-reduced (2.5 h) | | | (3) Sulfide-free (20 h) | | |
| 0[§] | 489 | 19.1 | 12 | 515 | 1.75 | 3.5 | 557 | 1.45 | 0 |
| 10[§§] | 83 | 32.95 | 0 | 79 | 2.52 | 0 | 127 | 0.53 | 0 |
| 20[§§] | 119 | 24 | 0 | 40 | 0.28 | 0 | 129 | 0.52 | 0 |
| | (4) ≈ 5 ppm $H_2S$ | | | (5) ≈ 10 ppm $H_2S$ | | | (6) ≈ 15 ppm $H_2S$ | | |
| 0[§] | 468 | 9.48 | 3.2 | 507 | 15.9 | 7.2 | 522 | 21.83 | 15 |
| 10[§§] | 114 | 6.27 | 0 | 121 | 15.83 | 0 | 121 | 22.96 | 4.2 |
| 20[§§] | 128 | 5.01 | 0 | 144 | 9.76 | 0 | 143 | 15.29 | 2.5 |

[§]Unfiltered
[§§]Measurements made on microfiltration permeate

These experiments indicate that $H_2S$ is involved in TS-hGH formation, and that stripping of $H_2S$ from the homogenised fermentation broth results in reduction (in sub-sample 2) or almost elimination (in sub-sample 3) of formation of TS-hGH in the microfiltered homogenate.

Example 2

Stripping of $H_2S$ in a fermentor

A sample comprising fermentation broth, recombinant microorganisms [*E. coli* containing an expression cassette comprising the gene encoding for recombinant human growth hormone (rhGH)] was taken from an hGH production batch and homogenized. 5 identical sub-samples were taken from the homogenized bulk sample. One of these sub-samples (sub-sample 1) was not subjected to stripping; the remaining 4 sub-samples were subjected to nitrogen-stripping [in a nitrogen-aerated (bubbled), stirred fermentor vessel (B. Braun Biostat™ CT; normal working volume 1 liter) with control of pH and temperature] using the conditions detailed in Table 2, below. Experiments 2 and 3 were performed without pH control, the pH value given in Table 2 being the initial value.

TABLE 2

| Experiment (sub-sample) | Aeration rate (vvm)[#] | Temperature (° C.) | Duration (min) | pH | Stirring speed (rpm) |
|---|---|---|---|---|---|
| 1 (control) | — | — | — | 8 | — |
| 2 | 1 | 20 | 95 | 8.5 | 1200 |

TABLE 2-continued

| Experiment (sub-sample) | Aeration rate (vvm)[#] | Temperature (° C.) | Duration (min) | pH | Stirring speed (rpm) |
|---|---|---|---|---|---|
| 3 | 0.25 | 20 | 30 | 7.6 | 600 |
| 4 | 0.25 | 20 | 60 | 7 | 600 |
| 5 | 0.25 | 20 | 1170 | 7 | 600 |

[#]volume of gas/volume of liquid/minute

The samples were then subjected to microfiltration as described in Example 1. Analysis for content of hGH and TS-hGH was likewise performed as described in Example 1. The results are shown in Table 3, below.

TABLE 3

| | Sub-sample | | | | | | | | | |
|---|---|---|---|---|---|---|---|---|---|---|
| | 1 | | 2 | | 3 | | 4 | | 5 | |
| Filtration time (min) | hGH (g/l) | TS-hGH (%) | hGH (g/l) | TS-hGH (%) | hGH (g/l) | TS-hGH (%) | hGH (g/l) | TS-hGH (%) | hGH (g/l) | TS-hGH (%) |
| 0[§] | 0.660 | 0.3 | 0.500 | 0 | 0.710 | 0.9 | 0.413 | 0.6 | 0.120 | 0 |
| 10[§§] | 0.105 | 13.0 | 0.290 | 0 | 0.113 | 3.1 | 0.062 | 0 | 0.004 | 0 |
| 20[§§] | 0.106 | 11.8 | 0.190 | 0 | 0.106 | 2.0 | 0.069 | 0 | 0.005 | 0 |

[§]Unfiltered
[§§]Measurements made on microfiltration permeate

The invention claimed is:
1. A method for reducing or substantially preventing formation of a trisulfide derivative of a polypeptide selected from recombinantly produced native human growth hormone (rhGH) and truncated forms thereof in a liquid medium containing said polypeptide, the method comprising stripping said liquid medium with a gas selected from the group consisting of nitrogen ($N_2$), helium (He), and argon (Ar), wherein said stripping is performed during post-production processing of said polypeptide, and wherein a sulfite or a mercapto compound is added to the liquid medium after production of said polypeptide.

2. A method according to claim 1, wherein said polypeptide is subjected to one or more purification steps after the stripping procedure.

3. A method according to claim 2, comprising at least one filtration step.

* * * * *

UNITED STATES PATENT AND TRADEMARK OFFICE
CERTIFICATE OF CORRECTION

| | | Page 1 of 1 |
|---|---|---|
| PATENT NO. | : 8,530,191 B2 | |
| APPLICATION NO. | : 12/714900 | |
| DATED | : September 10, 2013 | |
| INVENTOR(S) | : Peter Becker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 85 days.

Signed and Sealed this
Twenty-ninth Day of December, 2015

Michelle K. Lee
*Director of the United States Patent and Trademark Office*